(12) United States Patent
Strange

(10) Patent No.: US 6,328,045 B1
(45) Date of Patent: *Dec. 11, 2001

(54) PARTS WASHING SYSTEM

(75) Inventor: J. Leland Strange, Duluth, GA (US)

(73) Assignees: Chemfree Corporation, Norcross; Zymo International, Inc., Duluth, both of GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/567,939

(22) Filed: May 10, 2000

Related U.S. Application Data

(63) Continuation of application No. 09/515,731, filed on Feb. 29, 2000, which is a continuation of application No. 09/491,227, filed on Jan. 25, 2000, which is a continuation of application No. 09/097,439, filed on Jun. 15, 1998, which is a continuation of application No. 08/841,463, filed on Apr. 22, 1997, now Pat. No. 6,019,110, which is a continuation of application No. 08/315,902, filed on Sep. 30, 1994, now abandoned.

(51) Int. Cl.$^7$ .................................................. B08B 3/02
(52) U.S. Cl. ..................... 134/111; 134/155; 134/186; 134/169 A; 210/610; 435/264
(58) Field of Search ............................... 134/10, 11, 155, 134/186, 108, 19, 169 A, 110, 104.2; 210/610; 435/264

(56) References Cited

U.S. PATENT DOCUMENTS

| | | |
|---|---|---|
| 41,357 | 1/1864 | Best . |
| 168,052 | 9/1875 | Robinson . |

(List continued on next page.)

FOREIGN PATENT DOCUMENTS

| | | | |
|---|---|---|---|
| 1621604 | 9/1970 | (DE) . | |
| 2449056 | * 4/1976 | (DE) | ................................. 134/111 |
| 42 09 052 A | 2/1993 | (DE) . | |

(List continued on next page.)

OTHER PUBLICATIONS

Answer, Affirmative Defenses, Counterclaims and Demand for Jury Trial of Defendant James C. McClure—Chemfree Corporation v. James C. McClure—Civil Action No. 1 00–CV–15302—Mar. 16, 2001.

(List continued on next page.)

Primary Examiner—Frankie L. Stinson
(74) Attorney, Agent, or Firm—Womble Carlyle Sandridge & Rice

(57) ABSTRACT

Provided is a parts washer that includes a multi-tiered basin, a cleaning fluid and a biological component, living within the fluid, that breaks down organic waste. The multi-tiered basin includes a sink member with a false bottom, and a support grid and filter are interposed between the false bottom and a bottom panel of the sink member. The false bottom, support grid, and filter are readily removable from the sink member. The tank is partially filled with the cleaning fluid and a pump and conduit assembly direct a flow of the cleaning fluid to the basin. The cleaning fluid discharged into the basin flows through a drain hole in the false bottom, through the filter and support grid, and then through a drain hole in the bottom panel of the sink member back into the tank for reuse. The cleaning fluid includes, at least, a surfactant that functions to remove organic waste from the parts being washed. The biological component within the cleaning fluid includes nonpathogenic microorganisms that break down the organic waste. The cleaning fluid is not toxic to the microorganisms. The pump and conduit assembly, in addition to aiding in the removal of organic waste, functions to aerate the cleaning fluid to maintain a proper environment for the microorganisms. A heater, thermostat, and level control assembly function to maintain the cleaning fluid within a certain temperature range so as to aid in the removal of organic waste and maintain a proper environment for the microorganisms.

5 Claims, 3 Drawing Sheets

U.S. PATENT DOCUMENTS

| | | | |
|---|---|---|---|
| 1,382,915 | 6/1921 | Huggins . | |
| 1,556,913 | 10/1925 | Capra . | |
| 2,010,195 | 8/1935 | Meehan | 299/59 |
| 2,254,824 | 9/1941 | Large | 141/9 |
| 2,438,654 * | 3/1948 | Albertson | 134/111 |
| 2,573,008 | 10/1951 | Gorden | 134/111 |
| 2,573,128 * | 10/1951 | Cavicchioli | 134/110 |
| 3,279,605 | 10/1966 | Shepherd | 210/110 |
| 3,378,019 | 4/1968 | Riolo et al. | 134/111 |
| 3,476,600 | 11/1969 | Morgan, Jr. et al. | 134/111 |
| 3,477,361 | 11/1969 | Bradshaw | 99/408 |
| 3,522,814 * | 8/1970 | Olson | 134/111 |
| 3,662,890 | 5/1972 | Grimshaw | 210/195 |
| 3,707,404 | 12/1972 | Carlson et al. | 134/10 |
| 3,843,464 | 10/1974 | Usami et al. | 435/264 |
| 3,845,702 | 11/1974 | Mies | 99/408 |
| 3,890,988 * | 6/1975 | Lee | 134/111 |
| 3,923,540 | 12/1975 | Usami et al. | 435/264 |
| 3,960,728 * | 6/1976 | Otzen | 134/111 |
| 4,005,010 | 1/1977 | Lunt | 210/17 |
| 4,049,551 * | 9/1977 | Otzen | 134/11 |
| 4,087,356 | 5/1978 | Marconi et al. | 210/11 |
| 4,128,478 | 12/1978 | Metzger | 210/167 |
| 4,146,470 | 3/1979 | Mohan et al. | 210/2 |
| 4,226,548 * | 10/1980 | Retith | 134/111 |
| 4,230,562 | 10/1980 | Olivieri et al. | 210/610 |
| 4,284,509 | 8/1981 | Lindorfer et al. | 210/610 |
| 4,365,383 | 12/1982 | Bartlett | 15/302 |
| 4,382,873 | 5/1983 | Gatellier et al. | 252/312 |
| 4,414,333 | 11/1983 | Olivieri et al. | 435/243 |
| 4,452,894 | 6/1984 | Olsen et al. | 435/252.34 |
| 4,462,910 | 7/1984 | Lepain et al. | 210/610 |
| 4,464,256 * | 8/1984 | Plourde | 134/111 |
| 4,505,284 * | 3/1985 | Kyatt | 134/111 |
| 4,561,903 | 12/1985 | Blaul | 134/10 |
| 4,623,468 | 11/1986 | Lepain et al. | 210/749 |
| 4,713,343 | 12/1987 | Wilson, Jr. et al. | 435/264 |
| 4,727,031 | 2/1988 | Brown et al. | 435/244 |
| 4,746,434 | 5/1988 | Grieves et al. | 210/610 |
| 4,765,020 | 8/1988 | Weihe | 15/302 |
| 4,784,169 | 11/1988 | Striedieck | 134/111 |
| 4,811,791 | 3/1989 | Harnoy et al. | 166/305.1 |
| 4,822,490 | 4/1989 | Dyadechko et al. | 210/611 |
| 4,925,564 | 5/1990 | Francis | 210/610 |
| 5,019,174 | 5/1991 | Wallach | 134/40 |
| 5,107,876 | 4/1992 | Ozyjiwsky | 134/111 |
| 5,128,262 | 7/1992 | Undorger et al. | 435/264 |
| 5,132,224 | 7/1992 | Mueller et al. | 435/262 |
| 5,193,561 | 3/1993 | Robb et al. | 134/57 R |
| 5,209,851 | 5/1993 | Hume et al. | 210/610 |
| 5,217,616 | 6/1993 | Sanyal et al. | 210/617 |
| 5,225,083 | 7/1993 | Pappas et al. | 210/610 |
| 5,232,299 | 8/1993 | Hiss | 401/143 |
| 5,246,023 | 9/1993 | Breunsbach et al. | 134/111 |
| 5,303,725 | 4/1994 | Hilgren | 134/111 |
| 5,314,620 | 5/1994 | Staniec | 210/610 |
| 5,322,078 | 6/1994 | Tuttle | 134/105 |
| 5,339,845 | 8/1994 | Huddas | 134/169 |
| 5,364,789 | 11/1994 | Guinn et al. | 435/262.5 |
| 5,368,411 | 11/1994 | Losack | 405/128 |
| 5,376,183 | 12/1994 | Gatt et al. | 134/610 |
| 5,388,601 | 2/1995 | Mansur | 134/105 |
| 5,401,413 | 3/1995 | Gatt et al. | 210/610 |
| 5,427,128 | 6/1995 | Minkin | 134/105 |
| 5,454,878 | 10/1995 | Bala et al. | 134/10 |
| 5,458,747 | 10/1995 | Marks et al. | 204/130 |
| 5,464,533 * | 11/1995 | Koslow | 134/111 |
| 5,469,597 | 11/1995 | Page | 15/321 |
| 5,492,139 | 2/1996 | Lashmett et al. | 134/105 |
| 5,532,162 | 7/1996 | Aamont | 435/264 |

FOREIGN PATENT DOCUMENTS

| | | | |
|---|---|---|---|
| 0116151 * | 12/1982 | (EP) . | |
| 0309432 * | 9/1987 | (EP) . | |
| 0809432 | 9/1987 | (EP) | C11D/3/38 |
| 6254318 | 4/1994 | (JP) . | |
| 7-75795 | 3/1995 | (JP) . | |
| 2014286 | 6/1994 | (RU) . | |
| 475243 | 11/1937 | (SE) . | |
| 1496841 | 7/1989 | (SU) . | |

OTHER PUBLICATIONS

Obermer et al.—"Effects of the Addition of Microbial Surfactants on Hydrocarbon Degradation in a Soil Population In a Stirred Reactor"—Appl. Microb Biotechnol 32:485–489 1990.

GMF Industries, Inc. Papers/Brochures describing "Clam Parts Cleaning Systems and Mini–Wash Systems"—believed to be published before 10/93.

Brochure entitled "GSA, General Services Administration"—Nature Sorb of LA, Inc.—believed to be published before Apr. 1, 1993.

Taylor Environmental Products, Inc.—Papers/brochures describing "Big Red Taylor Gator Absorbent & Ent retech"—Believed to be published before 09/94.

Geoffrey H. Swett—Bioremediation: Myths vs. Realities—1992—pp. 23–26—Environmental Protection Magazine.

Brian N. Hicks & Jason A. Caplan, Ph.D.—Bioremediation: A Natural Solution, Jan. 15, 1993—Pollution Engineering Magazine—pp. 30–33.

Safety Kleen—Five Ways to Make a Tough Job Easier—1990—pp. 1–4—Sales Literature.

Microorganisms Sold as Part#LRC–1 by LA Remediation Co. of Motaire, LA.

Cleaning fluid Sold As Part#Sea Wash 7 by Warren Chemical Corp. of Robert Louisiana.

* cited by examiner

PARTS WASHING SYSTEM

CROSS REFERENCE TO RELATED APPLICATIONS

This application is a continuation of application Ser. No. 09/515,731, filed on Feb. 29, 2000, which is a continuation of application Ser. No. 09/491,227, filed on Jan. 25, 2000, which is a continuation of application Ser. No. 09/097,439, filed on Jun. 15, 1998, which is a continuation of application Ser. No. 08/841,463, filed on Apr. 22, 1997, now U.S. Pat. No. 6,019,110 which is a continuation of application Ser. No. 08/315,902, filed on Sept. 30, 1994 now ABN.

BACKGROUND OF THE INVENTION

The present invention relates generally to the field of cleaning and more particularly to the filed of parts washers.

Parts washers are well known and are often employed in the cleaning of parts that are contaminated with organic waste products such as, for example and not limitation, hydrocarbons, oils, and greases. For background and understanding, the type of parts normally being discussed as washed in a parts washer are, for example, automotive parts such as valves, pistons, transmission parts, covers, and so forth. Most conventional parts washers include basin mounted to the top of a tank. The tank is partially filled with a mineral spirits solvent that is pumped from the tank through a conduit that discharges into the basin where the parts are washed. The mineral spirits solvent drains from the basin back to the tank for reuse. A filter is sometimes interposed in the solvent flowpath to collect organic waste products and particulates washed from the parts.

While mineral spirits are an effective cleaning solvent, there are many drawbacks to the employment of parts washers that utilize mineral spirits. For example, some mineral spirit solvents are presently classified by government regulatory agencies as hazardous materials because of their low flash point and potential health concerns. Because of this classification, mineral spirits must be used, handled, and disposed of in compliance with extensive governmental regulations. Further, mineral spirits that are not properly contained can have a negative impact on the environment, and it is not uncommon for workers to have dermatitis and respiratory problems exacerbated by unprotected use of mineral spirits. Additionally, many users of mineral spirits find it necessary to dispose of used mineral spirits by having a waste disposal company pick up the used mineral spirits so that the used mineral spirits can be disposed of in compliance with the various governmental guidelines and regulations; such disposal can be expensive.

Filters are often incorporated into conventional parts washers to remove the organic waste products and particulates from the solvent. Thus, the filters eventually become saturated with the organic waste products and particulates and therefore need to be replaced. The filters are often difficult to access and replace. Furthermore, the filters, once they have absorbed the organic waste products, are often considered a hazardous material and are therefore difficult to dispose of.

There is, therefore, a need in the industry for a system and method which addresses these and other related, and unrelated, problems.

SUMMARY OF THE INVENTION

Briefly described, the present invention comprises a parts washing system characterized by a cooperative interaction among a mechanical component, fluid component, and biological component. The parts washer apparatus (herein also referred to as the "parts washer") of the parts washing system includes, in the preferred embodiment, a holding tank, cleaning fluid retained within the tank, microorganisms living with the cleaning fluid, a wash basin, a fluid delivery system and an in-line filter.

In accordance with the preferred embodiment of the present invention, the wash basin is a multi-tiered basin including a sink member defining a bottom panel and a false bottom disposed above the bottom panel. The multi-tiered basin further includes a support grid and filter interposed between the false bottom and the sink member; and the false bottom, support grid, and filter are readily removable from the sink member. The tank is partially filled with the cleaning fluid and a pump and conduit assembly direct a flow of the cleaning fluid to the basin. The cleaning fluid discharged into the basin flows through a drain hole in the false bottom, through the filter and support grid, and then through a drain hole defined through the bottom panel of the sink member and cleaning fluid is then returned to the tank for reuse.

In accordance with the preferred embodiment of the present invention, the cleaning fluid includes, at least, a surfactant that functions to remove organic waste from the parts being washed. The biological component includes microorganisms that digest the organic waste. The cleaning fluid is not toxic to the microorganisms such that the microorganisms survive and reproduce within the cleaning fluid environment. The pump and conduit assembly, in addition to aiding in the removal or organic waste, functions to aerate the cleaning fluid to maintain a proper environment for the sustainment of the microorganisms. A heater, thermostat, and level control assembly function to maintain the cleaning fluid within a certain temperature range so as to aid in the removal of organic waste and maintain a proper environment for the sustainment of the microorganisms. The microorganisms are preferably introduced into the cleaning fluid as spores (i.e., in a dormant state). The microorganisms in spore form are preferably adhered to the filter prior to use, and released from the filter when the cleaning fluid flows through the filter.

While the present invention is presented, for the most part, in the context of a system, the multi-tiered basin, in isolation, and the combination of the fluid component and biological component, in isolation, are each considered inventive.

It is therefore an object of the present invention to provide a new method, and apparatus for washing parts.

Another object of the present invention is to provide an "environmentally friendly" parts washing system.

Yet another object of the present invention is to decrease the production of hazardous waste materials.

Still another object of the present invention is to provide a parts washer that does not require frequent fluid replacement.

Still another object of the present invention is to provide a parts washer that breaks down organic waste into its non-contaminating components.

Still another object of the present invention is to sustain a biological component within a parts washer.

Still another object of the present invention is to provide a parts washer with a multi-tiered sink structure.

Still another object of the present invention is to provide a parts washer with a readily accessible and replaceable filter.

Still another object of the present invention is to greatly reduce (or eliminate) the need for disposal of organic waste washed from parts.

Still another object of the present invention is to wash parts and recycle resultant organic waste in a closed, self contained environment.

Still another object of the present invention is to provide a cleaning system that does not have a toxic effect on users.

Still another object of the present invention is to provide a parts washing system that does not employ a volatile and flammable cleaning fluid; whereby, contrary to that which is required for most, if not all, conventional parts washers, an automatically closing lid is not required on the parts washer of the present invention to isolate the cleaning fluid in the case of a shop fire.

Other objects, features and advantages of the present invention will become apparent upon reading and understanding this specification, taken in conjunction with the accompanying drawings.

DETAILED DESCRIPTION OF THE PREFERRED EMBODIMENT

Figure 1:
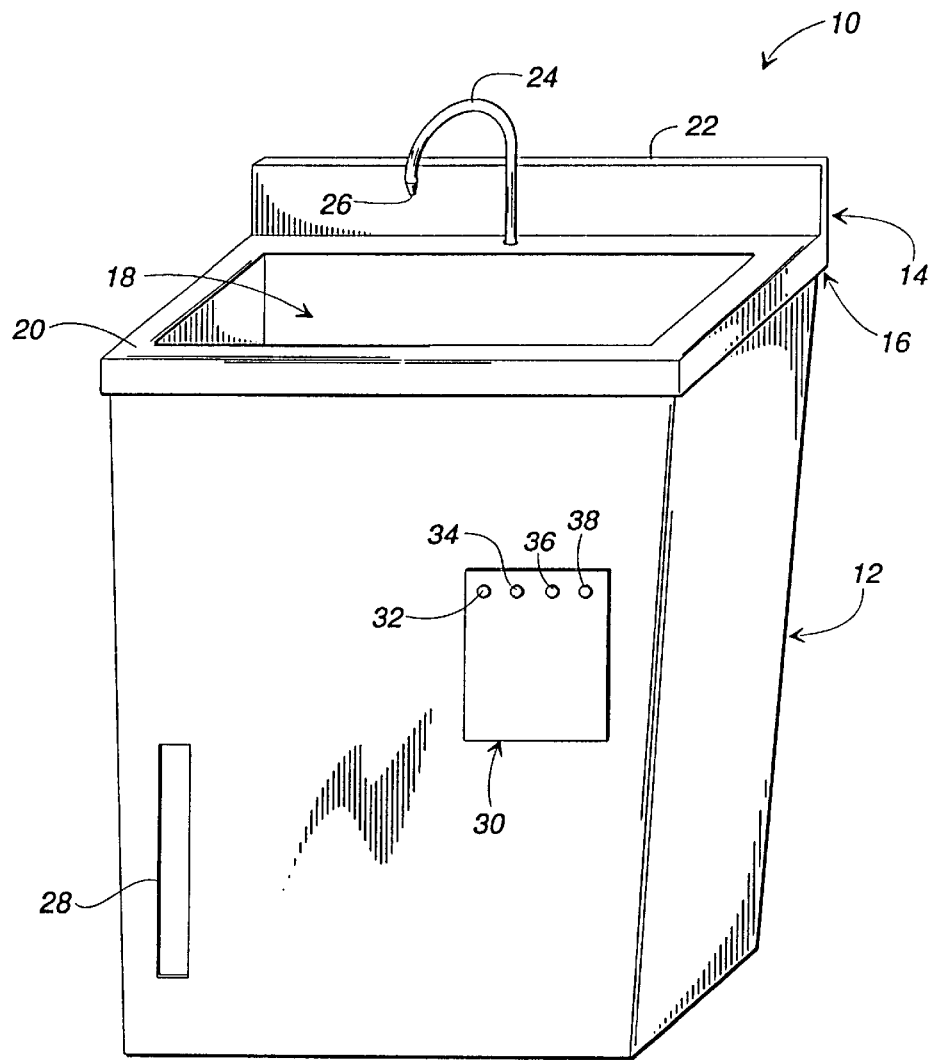
FIG. 1 is an exterior perspective view of a parts washer in accordance with the preferred embodiment of the present invention.

Referring now in greater detail to the drawings, in which like numerals represent like components throughout the several views, FIG. 1 is an exterior, perspective view of a parts washer apparatus (the "parts washer") 10, in accordance with the preferred embodiment of the present invention. The parts washer 10 includes a tank 12 and a basin 14. The basin 14 includes a sink member 16 that defines a basin cavity 18. The sink member includes a sink ledge 20 around the periphery of the inlet to the basin cavity 18. A back-splash 22 extends upward from a rear portion of the sink ledge 20, and a flexible faucet 24 penetrates the rear portion of the sink ledge 20 and terminates in the form of a nozzle 26. An optional work light (not shown) extends upward from the basin and illuminates the basin cavity 18. The tank 12 preferably includes a level indicator 28 and a control panel 30. The level indicator 28 is depicted as comprising a temperature sensitive, liquid crystal display. The control panel 30 includes an off/on switch 32, a power indicator light 34, a low fluid warning light 36, and a timer switch 38.

Figure 2:
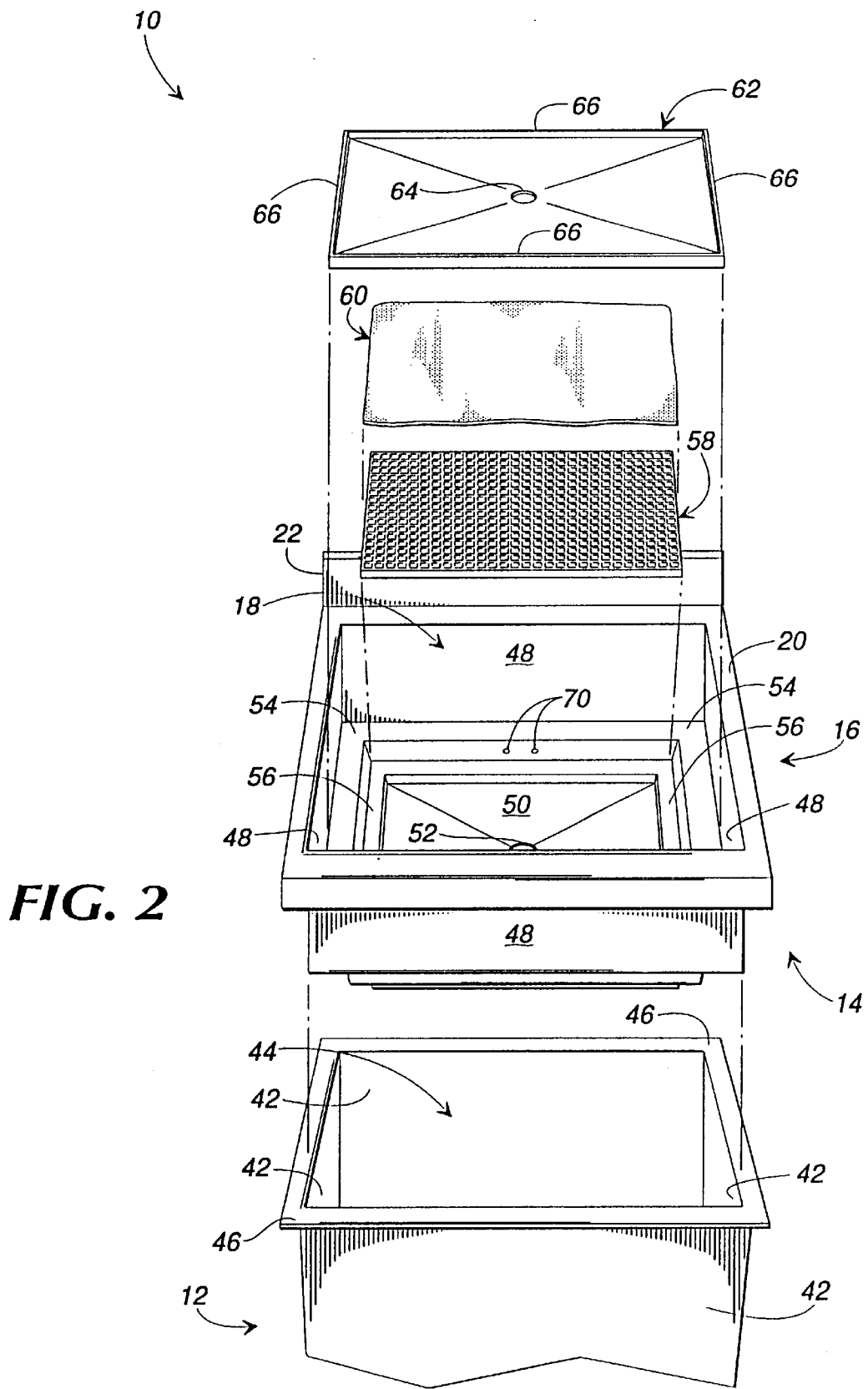
FIG. 2 is a cut-away, perspective, exploded view of isolated components of the parts washer of FIG. 1.

FIG. 2 is a cut-away, perspective, exploded view of certain components (mentioned below) of the parts washer 10, in accordance with the preferred embodiment of the present invention. A lower portion of the tank 12 is cut-away, and the faucet 24 and components associated with the lower portion of the tank 12 are not shown in FIG. 2. The tank 12 includes tank walls 42 that define a tank cavity 44 therebetween. The tank 12 further includes a tank lip 46 that extends around the periphery of the inlet to the tank cavity 44. The sink member 16 includes sink walls 48 extending downward from the sink ledge 20 to a bottom panel 50 that defines a drain hole 52 therethrough. The sink walls 48 and bottom panel 50 define the basin cavity 18. The sink walls 48 further define an upper ledge 54 and a lower ledge 56. Each of the ledges 54,56 encircle the basin cavity 18 and include four segments that together define a rectangular shape. Each edge of a planar, rectangular support grid 58 rest upon a segment of the lower ledge 56 such that the support grid 58 partitions the basin cavity. A rectangular filter pad 60 rests upon and covers the support grid 58. Each edge of a generally planar, rectangular false bottom member 62 rests upon a segment of the upper ledge 54 such that the false bottom member 62 also partitions the basin cavity 18 and is disposed above the support grid 58. The false bottom member 62 is preferably unitary, defines a drain hole 64 therethrough and includes an upwardly protruding lip 66 around the periphery thereof. A strainer (not shown) is defined within the drain hole 64. A pair of supplemental drain holes 70 are defined through the rear sink wall 48 just above the filter pad 60.

Figure 3:
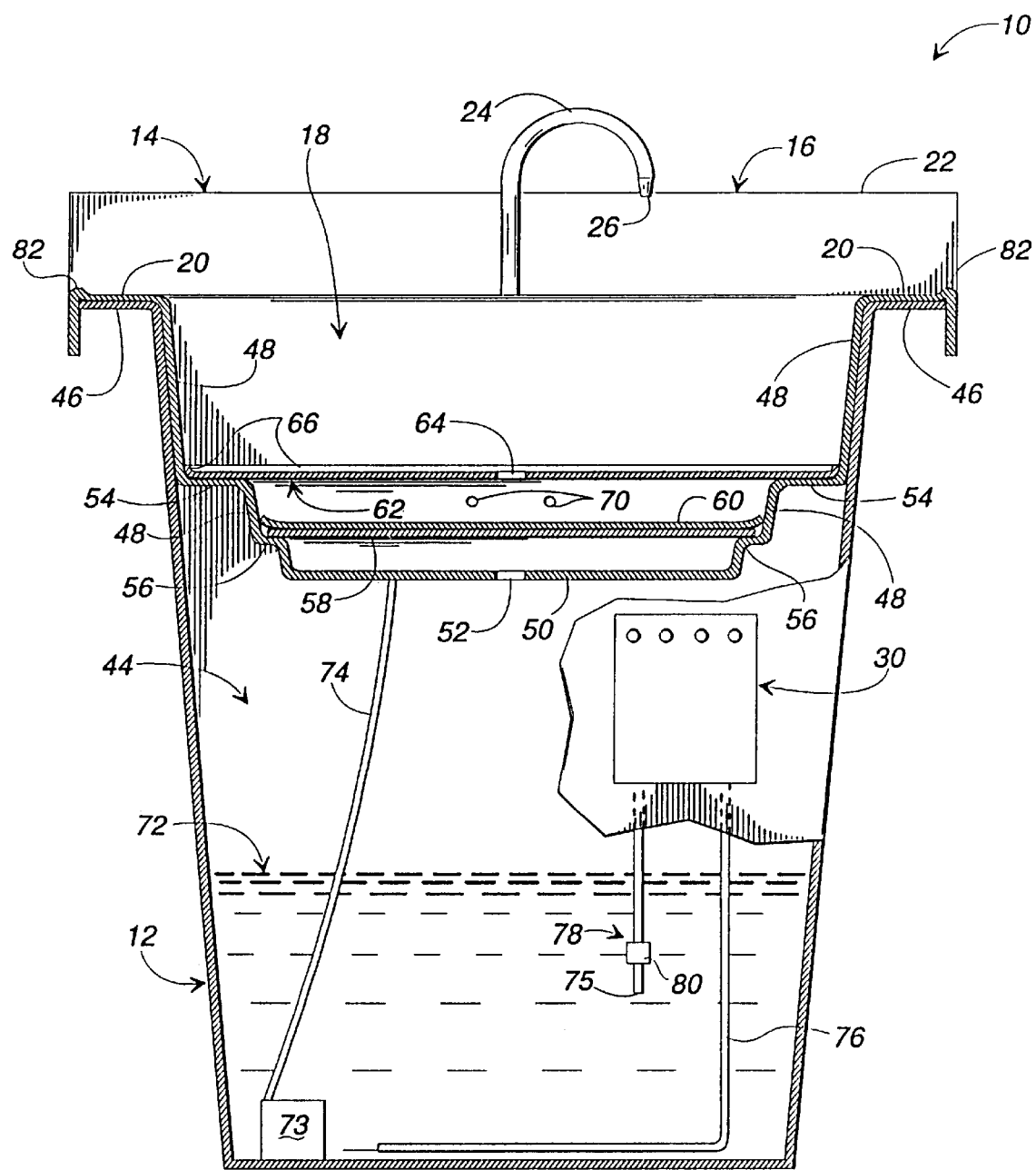
FIG. 3 is a front, vertical cross-sectional, cut-away view of the parts washer of FIG. 1, wherein certain portions of the parts washer are not cross-sectioned or cut-away.

FIG. 3 is a front, vertical cross-sectional, cut-away view of the parts washer 10, wherein certain portions of the parts washer are, for explanatory purposes, not cross-sectioned or cut-away. FIG. 3 represents each of the mechanical component (i.e., the hardware, or "parts washer" 10, as herein described), the fluid component (represented by a cleaning fluid 72), and the biological component (not seen) living within the cleaning fluid 72. As depicted in FIG. 3, the periphery of the false bottom member 62 preferably snugly contacts the sink walls 48. The tank cavity 44 is preferably partially filled with a cleaning fluid 72. A submersible pump 73 is disposed within the tank cavity 44. When the pump 73 is operating, it draws the cleaning fluid 72 from the bottom region of the tank cavity 44 and discharges the cleaning fluid 72 into a conduit 74. The conduit 74 is connected to and discharges into a base (not shown) of the faucet 24, whereby the fluid discharges from the nozzle 26. The parts washer 10 is preferably further equipped with optional cleaning accessories (not shown) such as a fountain brush (not shown) that is in fluid communication with the conduit 74. A heater 76, that is controlled by a thermostat 75, selectively heats the cleaning fluid 72, and the heater 76 is acceptably in the form of an electric heating element that extends from the control panel 30 into the depths of the tank cavity 44. A level probe monitors the depth of the cleaning fluid 72, and the level probe is acceptably in the form of a float actuated electric switch 78 that includes a magnet equipped float 80. A lip 82 extends around the periphery of the sink ledge 20 forward of the back-splash 22. The lip 82 and back-splash 22 seek to keep cleaning fluid 72 from dripping over the edges of the sink ledge 20. In accordance with the presently preferred construction of the present invention, much of the parts washer 10 is acceptably constructed from high density polyethylene. In addition, the sink walls 48, bottom panel 50, upper ledge 54, lower ledge 56, sink ledge 20, and backsplash 22, are, in accordance with the presently preferred construction, formed as a single, molded, unitary piece.

The biological component is preferably in the form of microorganisms that biodegrade organic compounds such as, for example and not limitation, hydrocarbons, oils, greases, petroleum by-products, creolates, polychlorinated biphenols, and other carbon based compositions. For example, the microorganisms convert hydrocarbon compounds into elements of water, carbon dioxide, and other digestion products. The microorganisms employed preferably not only have the capability of biodegrading organic waste, but further are resistant to environmental shock and have metabolic versatility. Additionally, the microorganisms are preferably nonpathogenic. Acceptable microorganisms, for example and not limitation, are those from the genera Bacillus, Pseudomonas, and Flavobacterium. Suitable species are well known and reported in the art. The microorganisms preferably range in size from approximately three to five microns, whereby they readily pass through the filter pad 60. The microorganisms are preferably employed in combination with nitrifying or denitrifying bacteria, phosphate solubilizing strains of microorganisms, bio-emulsifer producing strains of microorganisms, and strains of microorganisms which produce growth factors such as, for example and not limitation, B-vitamins.

The microorganisms are preferably subjected to a preservation technique in an effort to ensure their viability in the field, their viability while remaining in spore form for extended periods, and their resistance to environmental shock. For example, nutrient and buffer components such as, for example and not limitation, agar, and water soluble adhesives such as, for example and not limitation, gum, are preferably mixed with the microorganisms to promote stability of the microorganisms prior to mixing the microorganisms with a carrier. The carrier is, for example and not limitation, acceptably an inert and nutrient organic material such as, but not limited to, heat treated, expanded, cellulose material. The carrier preferably preserves and protects the microorganisms in spore form during storage and transportation. In accordance with the preferred embodiment of the present invention, an acceptable example of the microorganisms is available from the Louisiana Remediation Company, located in Motaire, La., as part number LRC- 1.

Figure 4:
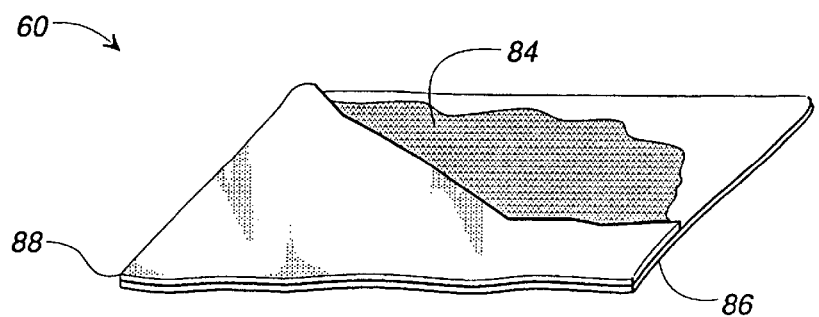
FIG. 4 is a perspective, cut-away view of a filter pad portion of the parts washer in accordance with the preferred embodiment of the present invention.

In accordance with the preferred embodiment of the present invention, the filter pad 60 functions as a vehicle for bringing the microorganisms in spore form into contact with the cleaning fluid 72. The filter pad 60 is acceptably constructed, for example and not limitation, from cotton, cellulose, polyolefin fibers, polyester fibers, fiberglass, or the like. Additionally, the filter pad 60 is acceptably constructed from combinations of such components. Further, the filter pad 60 is acceptably a ten micron filter or larger. In accordance with the preferred embodiment of the present invention, microorganisms in spore form are attached to the filter pad 60 with an adhering agent 84 (FIG. 4) that is water soluble and releases the microorganisms when the cleaning fluid 72 is introduced to the filter pad 60, as discussed below. Referring to FIG. 4, which is a perspective, cut-away view of the filter pad 60 in accordance with the preferred embodiment of the present invention, the filter pad 60 includes a layer 86 of inert material that is disposed below a layer 88 of micron-rated media. The inert material is acceptably fiberglass. The micron-rated media is preferably a material that does not have an affinity for hydrocarbons such as, for example and not limitation, polyester. The microorganisms in spore form, the components mixed therewith as discussed above, and the adhering agent 84 are preferably sandwiched between the layers 86,88 of the filter pad 60. A portion of the layer 88 is cut-away for explanatory purposes in FIG. 4 such that the adhering agent 84 is seen. In accordance with the preferred embodiment of the present invention, an acceptable adhering agent 84 is "Super 77 Spray Adhesive", which is available from the 3M Corporation of St. Paul, Minn. Once the microorganisms in spore form are attached to the filter pad 60, the filter pad 60 is acceptably stored until its usage within the parts washer 10 is desired. In accordance with an alternate embodiment of the present invention, the microorganisms are added directly to the cleaning fluid 72 without being initially attached to the filter pad 60. Thus, the filter pad 60 functions, in accordance with the preferred embodiment, as both a mechanical filter (i.e., straining particulate matter from the fluid 72) and as an initial transport medium for the microorganisms; and in an alternate embodiment, the filter pad 60 functions solely as a mechanical filter.

In accordance with the preferred embodiment of the present invention, the cleaning fluid 72 is compatible with (i.e., is non-toxic to) the microorganisms such that the microorganisms are capable of living within the cleaning fluid 72. Additionally, the cleaning fluid 72 tends to remove organic waste from parts washed in the basin 14, as will be discussed in greater detail below. An acceptable cleaning fluid 72, for example and not limitation, is a mixture of pH neutral emulsifiers and surfactants containing no volatile organic compounds, phosphates, formaldehyde, biocides, or other toxic materials. The emulsifier and surfactants are blended in liquid form to produce a biodegradable, non-toxic, non-caustic, non-flammable oil dispersant cleaner and degreaser. Further, and for example and not limitation, the exemplary acceptable cleaning fluid 72 contains no known carcinogens, no OSHA (Occupational Health and Safety Act) or DOT (United States Department of Transportation) regulated chemicals, no ingredients requiring SARA (Superfund Amendments and Reauthorization Act) Title III reporting, no RCRA (Solid Waste Disposal Act as amended by the Resources and Conservation Recovery Act of 1976 as amended),hazardous waste chemicals, and no items on the CERCLA (Comprehensive Environmental Response, Compensation and Liability Act) hazardous substance list (based upon the relevant regulations at the time this application was filed). Additionally, and for example and not limitation, the exemplary cleaning fluid 72 is a freely flowing liquid with a specific gravity of 1.083, a slight pleasant odor, no flash point, a boiling point of 210° Fahrenheit, a pH of approximately seven, and which is infinitely soluble in water. In accordance with the preferred embodiment of the present invention, an acceptable example of the cleaning fluid 72 is available from Warren Chemical Corporation of Robert, La., as part number SeaWash 7.

Referring further to FIG. 3, in operation, the pump 73, conduit 74, and faucet 24 circulate cleaning fluid 72 from the depths of the tank cavity 44 to the basin cavity 18 where parts cleaning takes place. The false bottom member 62 is preferably sufficiently sturdy and well supported such that a variety of parts are capable of being placed thereon for cleaning. In accordance with one method of the present invention, cleaning fluid 72 flows out of the nozzle 26 and the part being washed is oriented within the stream of cleaning fluid 72 exiting the nozzle 26. The cleaning fluid 72 removes organic waste from the part being washed, and then the cleaning fluid 72, along with the organic waste and any small particulate washed from the part, flows by gravity through the drain hole 64 and the strainer (not shown) associated therewith. The strainer will, of course, keep certain objects from passing through the drain hole 64. The cleaning fluid 72, organic waste, and remaining particulate matter then encounter the filter pad 60. Subsequently, the fluid 72 and organic contaminants pass through the support grid 58, and drain hole 52 to deposit into the tank cavity 44. Should flow through the filter pad 60 become obstructed, flow will divert through the pair of supplemental drain holes 70 defined through the rear sink wall 48 just above the filter pad 60. The filter pad 60 preferably functions to trap the particulate matter and allow the organic contaminants and cleaning fluid 72 to pass therethrough. Because the filter pad 60 does not collect the organic contaminant, it is capable of being disposed of as a solid waste.

If the filter pad 60 is new or relatively new such that all of the microorganisms in spore form have not been previously released therefrom, the cleaning fluid 72 releases dormant microorganisms attached to the filter pad 60, and the released microorganisms flow with the cleaning fluid 72 and organic contaminants through the drain hole 52 into the tank cavity 44. Within the tank cavity 44, a large percentage of the microorganisms and organic contaminants will tend to accumulate proximate to the surface of the cleaning fluid 72 such that a large portion of the biodegradation takes place proximate to the surface of the cleaning fluid 72. In theory, this forms a sort of vapor barrier that tends to minimize the evaporation of the cleaning fluid 72. If living microorganisms are not present in the parts washer 10, increasing amounts of organic waste will accumulate toward the surface of the cleaning fluid 72 in the tank cavity 44, and this condition is indicative of the need to replenish the microorganisms. In theory, however, if the parts washer 10 is used for normal parts cleaning, new microorganisms should never need to be added to the cleaning fluid 72 of the parts washer 10. Nonetheless, by virtue of the fact that the filter pad 60 is the vehicle for adding the microorganisms to the cleaning fluid 72, as discussed above, microorganisms are added to the cleaning fluid 72 each time a new filter pad 60 is added to the parts washer 10, as discussed in greater detail below. By virtue of the microorganisms digesting the organic waste within the tank 12, the cleaning fluid 72 is "recycled" within the parts washer 10, whereby the cleaning fluid 72 has the potential to last for extended periods of time. It is likely, however, that some cleaning fluid 72 replenishment will be required, however, to make up for evaporative and "dragout" losses incurred as parts are removed from the basin cavity 18 in wet condition. Furthermore, by virtue of the cooperative effect of the filter pad 60 (removing particulate matter) and the microorganisms (digesting organic waste), the tank is, potentially, seldom in need of "dredging" to remove waste. The pump 73 is preferably proximate to the bottom of the tank 12 such that any sludge that might tend to accumulate at the bottom of the tank cavity 44 is circulated through the filter pad 60.

Referring back to FIGS. 1 and 3, when the off/on switch 32 is in the "on" position, electricity is supplied to circuitry (not shown) which is housed within the control panel 30 by way of a conventional power cord (not shown), and the indicator light 34 is illuminated. In accordance with the preferred embodiment of the present invention, once the off/on switch 32 is in the "on" position, the circuitry, in combination with the thermostat 75, will activate and deactivate the heater 76. While the thermostat 75 senses that the temperature of the cleaning fluid 72 within the tank cavity 44 is below a desired temperature, the heater 76 is on, and while the thermostat 75 senses that the temperature of the cleaning fluid 72 is at or above the desired temperature, the heater 76 is off The cleaning fluid 72 is preferably maintained in a temperature range which supports the lives of the particular microorganisms employed within the parts washer 10. In accordance with the preferred embodiment of the present invention, the temperature is acceptably maintained in the range of approximately 110° to 115° degrees Fahrenheit. The float actuated electric switch 78 also controls the operation of heater 76. When the magnet equipped float 80 drops downward due to a low level of cleaning fluid 72, the switch 78 is actuated which, in combination with the circuitry, disables the heater 76 and causes the low level warning light 36 to illuminate. Operation of the pump 73 is controlled by the timer switch 38. A user can manually actuate the timer switch 3 8 which, in combination with the circuitry, causes the pump 73 to operate and automatically cut off after a certain period of time. In accordance with an alternate embodiment of the present invention, an additional switch (not shown) is provided that overrides the timer switch 38 such that the pump 73 will remain running as long as the additional switch is "on".

Referring back to FIGS. 2 and 3, the parts washer 10 is designed to provide easy access to the filter pad 60. Access is obtained by simply lifting the false bottom member 62 out of the basin cavity 18. In accordance with the preferred embodiment of the present invention there is no restrictive engagement between any of the components that are depicted as exploded away from each other in FIG. 2, whereby the components of the parts washer 10 are readily accessible.

While certain of the preferred and alternate embodiments of the present invention have been disclosed herein, other embodiments of the apparatus and methods of the present invention will suggest themselves to persons skilled in the art in view of this disclosure. Therefore, it will be understood that variations and modifications can be effected within the spirit and scope of the invention and that the scope of the present invention should only be limited by the claims below. Additionally, while it is intended that the scope of the present invention also include various alternate embodiments, it should be understood that each of the embodiments disclosed herein, including the preferred embodiment, includes features and characteristics which are considered independently inventive. Accordingly, the disclosure of variations and alterations expressed in alternate embodiments is intended only to reflect on the breadth of the scope of the present invention without suggesting that any of the specific features and characteristics of the preferred embodiment are in any way obvious or unimportant.

I claim:

1. In a combination for cleaning hydrocarbons from a part, the combination comprising hydrocarbon biodegrading microorganisms, a cleaning fluid that is not toxic to the microorganisms, a washing apparatus including a tank for containing the fluid and a basin for receiving the part, a pump and conduit assembly for pumping the fluid from the tank into contact with the part within the basin, and a flowpath defined between the basin and the tank through which the fluid flows from the basin back to the tank, an improvement thereto comprising:

a filter interposed within the flowpath for delivering the microorganisms into the fluid.

2. The combination of claim 1, wherein said filter is constructed and arranged so that the hydrocarbons substantially pass through said filter, whereby said filter does not collect a substantial amount of hydrocarbons, whereby said filter is capable of being disposed of as a solid waste.

3. The combination of claim 2, wherein said microorganisms have a dormant state, and wherein said microorganisms in said dormant state are adhered to said filter.

4. The combination of claim 2, further comprising an adhering means for adhering said microorganisms to said filter, and releasing said microorganisms adhered to said filter into the fluid.

5. The combination of claim 4, wherein said adhering means is a water soluble adhesive.

\* \* \* \* \*